(12) United States Patent
Matsutani et al.

(10) Patent No.: US 6,837,896 B2
(45) Date of Patent: Jan. 4, 2005

(54) MEDICAL BLADED DEVICE

(75) Inventors: Kanji Matsutani, Tochigi-ken (JP); Takashi Ina, Tochigi-ken (JP)

(73) Assignee: Mani, Inc., Tochigi-ken (JP)

( * ) Notice: Subject to any disclaimer, the term of this patent is extended or adjusted under 35 U.S.C. 154(b) by 14 days.

(21) Appl. No.: 10/153,705

(22) Filed: May 24, 2002

(65) Prior Publication Data

US 2003/0004527 A1 Jan. 2, 2003

(30) Foreign Application Priority Data

May 25, 2001 (JP) ........................................ 2001-156492

(51) Int. Cl.[7] .............................................. A61B 17/32
(52) U.S. Cl. ....................................... 606/167; 30/346
(58) Field of Search ................................ 606/166, 167, 606/170, 223; 604/158, 160, 187; 30/346.57, 353, 346, 348

(56) References Cited

U.S. PATENT DOCUMENTS

| | | | |
|---|---|---|---|
| 4,911,714 A | * | 3/1990 | Poley .......................... 623/6.18 |
| 5,100,390 A | * | 3/1992 | Lubeck et al. .............. 604/158 |
| 5,749,897 A | * | 5/1998 | Matsutani et al. .......... 606/222 |
| 5,967,012 A | * | 10/1999 | Dummer et al. .............. 83/451 |
| 6,214,030 B1 | * | 4/2001 | Matsutani et al. .......... 606/223 |
| 6,554,840 B2 | * | 4/2003 | Matsutani et al. .......... 606/107 |

* cited by examiner

Primary Examiner—Julian W. Woo
(74) Attorney, Agent, or Firm—Townsend & Banta

(57) ABSTRACT

A medical bladed device is provided containing a handle and a cutting blade portion which is tapered and formed in continuation from the handle and having first and second faces on a front face, and third and fourth faces on a back face with a pair of primary cutting blades, each formed on both sides thereof, and a pair of secondary cutting blades, each formed on both sides thereof, the cutting blade having a sharp tip and being formed with a triangular cross section by forming a fifth face diagonally crossing from the front face of the cutting blade portion to the back face of the cutting blade portion. A secondary cutting blade angle is formed by the pair of secondary cutting blades ranging from 35 to 105 degrees, and a primary cutting blade angle is formed by an imaginary intersecting point between the pair of primary cutting blades ranging from 15 degrees to 35 degrees.

8 Claims, 6 Drawing Sheets

MEDICAL BLADED DEVICE

BACKGROUND OF THE INVENTION

1. Field of the Invention

The present invention relates to a medical bladed device having a quadrangular pyramid shaped cutting blade portion formed thereto, and more particularly to a medical bladed device which provides excellent cutting performance during incision of living body tissue, inexpensiveness, and high endurance.

2. Description of Related Art

A medical bladed device has a function of forming a primary incision to a living body tissue by using a sharp tip portion thereof or by using a sharp cutting blade thereof, and has also a function of cutting open a living body tissue having a primary incision formed thereto by using a cutting blade thereof. The cutting performance of the medical bladed device is determined by the counterforce arisen during the forming of the primary incision and the counterforce arisen during the incising of the living body tissue.

More particularly, a medical bladed device having a cutting blade portion formed on a tip-side thereof with a quadrangular (e.g., rhombus shape) cross section is purposed for piercing, incising, or cutting off an extremely unsteady affected area with delicate manipulation of the finger tips by a careful operator, and has a sharp tip portion formed thereto, in which each side comprising the quadrangular shape is concentrated at the tip portion, thereby the sharp tip portion pierces a targeted living body tissue and a cutting blade extending from the tip portion passes through the living body tissue to: widen or cut off the targeted area.

Examples of the medical bladed device are a medical knife used in brain surgery, a medical knife used in ophthalmologic surgery for forming an incision by incising the cornea or a space between the cornea and the sclera, or a suture needle for suturing an incision. A good cutting performance, which includes a property of having little pierce counterforce when piercing a living body tissue and a property of having little incision counterforce when cutting open a living body tissue, and also rigidity (inflexibility), which is desired by physicians in handling a living body tissue are required for delicately manipulating the medical bladed device; in addition, other properties, such as excellent endurance against extensive repetitive use and inexpensiveness are also required.

Medical knives or suture needles, for example, used in ophthalmologic surgery have a tip portion being narrowly sharpened for enhancing piercing performance. However, narrowly sharpening the tip portion causes loss of endurance since the rigidity (inflexibility) of the tip portion decreases in association with narrowing and sharpening the tip portion. Furthermore, depending on the living body tissue, the tip portion will be unable to pierce if the tip portion is narrowly sharpened too excessively. Such problems prevents a physician from desirably performing an incising procedure, causes enormous stress for the physician, and may adversely affect proceeding of an operation.

When the cutting blade portion formed proximally to a tip-side has a quadrangular shaped cross section, a sharp peak, which has four sides (ridgelines forming the cutting blade and the back) matching at the tip, is required to be formed thereto for enhancing piercing performance. However, the process of matching the four sides at a single point causes increase in manufacture cost since device(s) for such process and product(s) are required to be controlled with extreme delicacy. Therefore, the tip portion, in actual circumstance, is corrected by hand after the tip portion and the cutting blade portion extending from the tip portion are processed.

The present applicant has already developed a technology relating to a suture needle capable of solving the aforementioned problems and has obtained a patent (Japanese Patent No. 1850827) thereof. This technology relates to a bladed suture needle having a three-faced tip portion, in which a quadrangular pyramid-like bladed suture needle has a three-faced tip portion consisted of two adjacent faces and one face formed by grinding or polishing two remaining faces of the quadrangular pyramid-like bladed suture needle. By forming the three-faced tip portion, the suture needle can have a triangle shaped cross section with the three faces constituting the triangle matched precisely at a peak portion for enabling excellent piercing performance.

In manufacturing the suture needle, two faces of a quadrangular pyramid-shaped portion are grinded or polished toward the remaining two sides of the quadrangular pyramid-shaped portion, so that a peak can be formed where each side is matched at the peak. This method is extremely simple compared to a method of polishing or grinding each four faces, so that a peak can be formed where four ridgelines formed between each face is matched at the peak. Accordingly, manufacture cost will not rise and a suture needle having excellent piercing performance can be provided.

An attempt of applying the same technology of the suture needle for manufacturing a medical bladed device (including a medical knife) based on the technology revealed some problems. That is, the medical bladed device being applied with such technology revealed a problem in manipulability owing to the shape of the three faced tip portion, wherein in some cases the medical bladed device can provide excellent manipulability with excellent cutting performance and high inflexibility, while in other cases the medical bladed device is unable to provide excellent cutting performance, or the medical bladed device, though being capable of providing satisfactory cutting performance, displays low inflexibility. That is, the medical bladed device revealed poor balance between cutting performance and inflexibility, lack of; consistency in performance, and difficulty in performing steady manipulation.

For example, piercing performance of the medical bladed device deteriorates and leads to a problem of poor cutting performance (including piercing performance) when the angle formed by two cutting blades among the three faces of the tip portion (cutting blade portion) become exceedingly larger than that of the cutting blades of the quadrangular pyramid shaped portion or when the three faced portion of the tip portion make up a large portion of the quadrangular pyramid shaped portion. Conversely, inflexibility decreases and leads to adverse results in manipulability when the angle formed by cutting blades of the tip portion become exceedingly small.

It is an object of the present invention to provide a medical bladed device for improving cutting performance and manipulability upon living body tissue and for improving endurance while preventing rise in manufacture cost.

SUMMARY OF THE INVENTION

For solving the aforementioned problems, the inventor(s) of the present invention has performed an experiment for applying the technology of the suture needle to a medical bladed device (including a medical knife, a suture needle). In this experiment, various test pieces of medical knives were prepared in search for better cutting performance.

Cutting performance of medical bladed devices can be judged qualitatively based on the pierce counterforce felt by a manipulating physician during piercing of a living body tissue in forming a primary incision and the incision counterforce felt by the manipulating physician during widening of the primary incision. In addition to the cutting performance, inflexibility based on the flexibility of the bladed device during incision of the living body tissue is also a large factor for judgment when the medical bladed device is actually used for incising the living tissue, but is however a factor often depending on the preference of the physician.

The inventor(s) of the present invention with the cooperation of several physicians has experimented the cutting performance of the medical bladed device and has found that, although slightly dispersed depending on the physician, the bladed device is judged to have "poor cutting performance" when pierce counterforce and incision counterforce exceeds from 190 mN (milli-Newtons) to 200 mN. It is now to be noted that "cutting performance" is strongly related to controllability (manipulability) of the bladed device. Furthermore, the manipulability of the bladed device is an extremely vital element since the manner in recovery differs largely by the state of an incision formed when the bladed device of this invention is, for example, used upon a portion of an eyeball such as the cornea or the sclera.

A polyurathane sheet (Registered trademark: Porvair) with a thickness of 0.45 mm being widely employed as a piercing material for ophthalmologic purposes was used in the experiment in a state where the piercing material was dampened in a uniformly maintained temperature; in the experiment the cutting performance of the bladed device was judged quantitatively from the maximum force created when a testpiece being attached to a jig was pressed upon the piercing material, had a tip thereof pierced through the piercing material, and advanced until reaching to a depth of a cutting blade portion proximal to a shank-side. That is, the cutting performance was judged from the value obtained by measuring the maximum value of pierce counterforce and incision counterforce arisen when the testpiece was pierced and advanced through the piercing material.

An eyeball of a swine was used for creating a state similar to ophthalmologic surgery and was pierced and incised by a same operator, so that inflexibility could be judged from the feedback felt during such procedure. Accordingly, inflexibility is to be judged qualitatively.

The testpieces used in the experiment were produced by combining the following angles, in which one angle (tip angle) formed by two cutting blades on both ends of the long sides of a tip-side cutting blade portion with a triangular cross-section situated proximal to a tip-side was stepped every 10 degrees between a range of 30 degrees to 110 degrees, and the other angle (blade angle) formed by two cutting blades on a shank-side cutting blade portion with a quadrangular cross-section situated proximal to a shank-side was stepped every 5 degrees between a range of 20 degrees to 30 degrees.

The results of the experiment are shown in table 1. Table 1 shows that cutting performance is greater as the blade angle and the tip angle become smaller, and poorer as the blade angle and the tip angle become larger. That is, the maximum value of the pierce counterforce and incision counterforce become larger and cutting performance becomes greater as both angles become smaller, and the maximum value of the pierce interforce and incision counterforce become smaller and cutting performance becomes poorer as both angles become larger.

Since the tip becomes narrower and sharper as the blade angle and the tip angle become smaller, the tip becomes easier to flex and inflexibility would decrease.

TABLE 1

| | Tip angle (°) | Blade angle (°) | Difference (°) | Cutting Performance (mN) | Inflexibility |
|---|---|---|---|---|---|
| 1 | 30 | 20 | 10 | 72 | X |
| 2 | 40 | | 20 | 79 | Δ |
| 3 | 50 | | 30 | 111 | ○ |
| 4 | 60 | | 40 | 127 | ○ |
| 5 | 70 | | 50 | 126 | ○ |
| 6 | 80 | | 60 | 144 | ○ |
| 7 | 90 | | 70 | 165 | ○ |
| 8 | 100 | | 80 | 192 | ○ |
| 9 | 30 | 25 | 5 | 78 | X |
| 10 | 40 | | 15 | 89 | X |
| 11 | 50 | | 25 | 90 | ○ |
| 12 | 60 | | 35 | 121 | ○ |
| 13 | 70 | | 45 | 138 | ○ |
| 14 | 80 | | 55 | 150 | ○ |
| 15 | 90 | | 65 | 166 | ○ |
| 16 | 100 | | 75 | 191 | ○ |
| 17 | 110 | | 85 | 221 | ○ |
| 18 | 40 | 21 | 10 | 81 | X |
| 19 | 50 | | 20 | 103 | Δ |
| 20 | 60 | | 30 | 134 | ○ |
| 21 | 70 | | 40 | 148 | ○ |
| 22 | 80 | | 50 | 151 | ○ |
| 23 | 90 | | 60 | 171 | ○ |
| 24 | 100 | | 70 | 173 | ○ |
| 25 | 110 | | 80 | 234 | ○ |

Resulting from the experiment, a particular relation between the tip angle and the blade angle has been found for demonstrating a satisfactory cutting performance (including piercing performance upon a living body tissue) as well as high inflexibility for enduring manipulation during an operation. That is, despite having a satisfactory cutting performance, inflexibility would be low and cause a risk of unsteady manipulation during an operation when the difference between the tip angle and the blade angle is smaller than 20 degrees. Therefore, the difference between the tip angle and the blade angle should preferably be 20 degrees or more.

Table 1 shows that cutting performance becomes 180 mN or more when the difference between the tip angle and the blade angle is no less than 75 degrees or no less than 80 degrees. Accordingly, considering, for example, dispersion or preferences :of physicians, the difference between the tip angle and the blade angle should preferably be no more than 70 degrees when used as a medical bladed device.

The foregoing medical bladed device provides satisfactory cutting performance and flexibility, and demonstrates excellent manipulability. More particularly, inflexibility is related to flexibility when piercing and cutting open a living body tissue. That is, low inflexibility signifies that a cutting blade portion is easy to flex, and high inflexibility signifies that a cutting blade portion is difficult to flex. Therefore, the strength of the medical bladed device is related to inflexibility, and the medical bladed device can demonstrate endurance for enduring repetitive numerous use by having inflexibility of a moderate degree. A satisfactory manipulability can be obtained by selecting a suitable balance between cutting performance and inflexibility.

BRIEF DESCRIPTION OF THE DRAWINGS

The above and other objects and features of the invention are apparent to those skilled in the art from the following preferred embodiments thereof when considered in conjunction with the accompanied drawings, in which.

DESCRIPTION OF THE PREFERRED EMBODIMENTS

Figure 1:
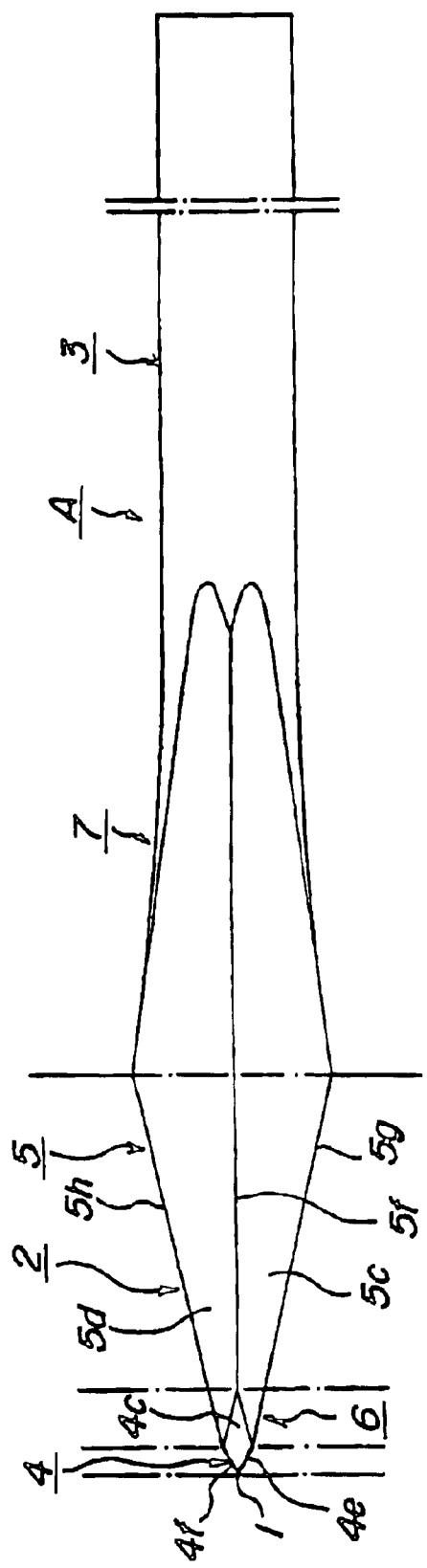
FIG. 1 is a front view for explaining the structure of a bladed device.
Figure 2A:
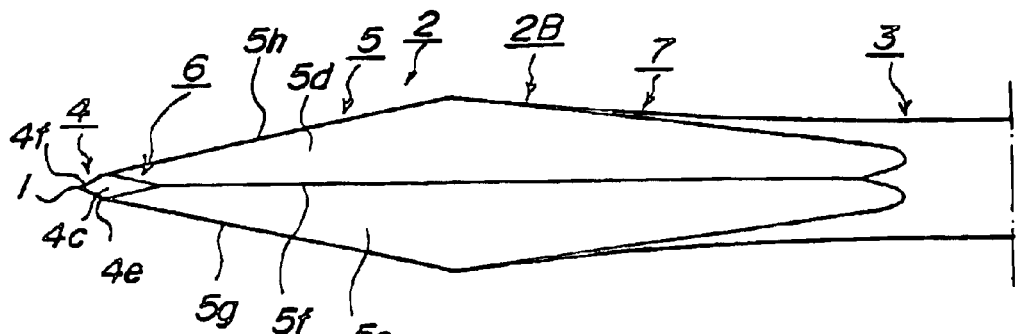
FIG. 2 is a four-face view for explaining the shape of an essential portion of a bladed device.
Figure 2B:
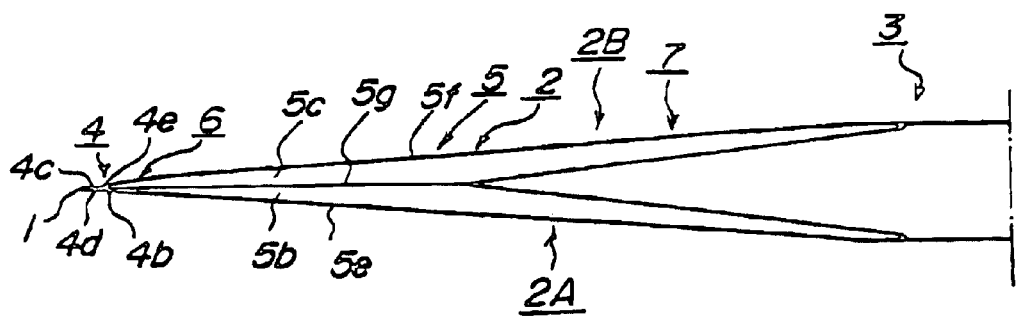
Figure 2C:
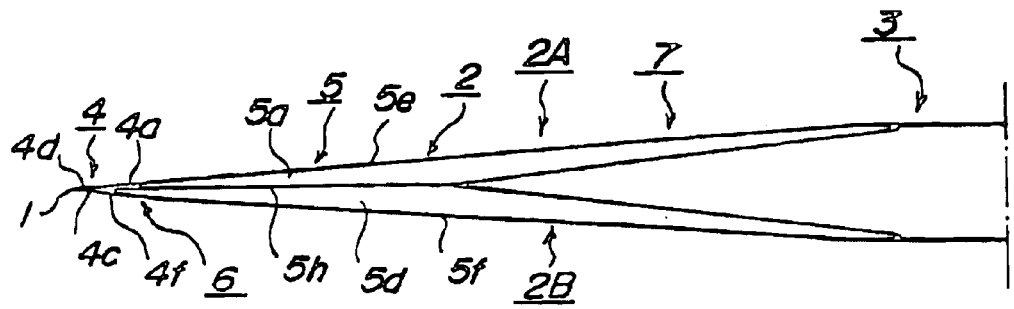
Figure 2D:
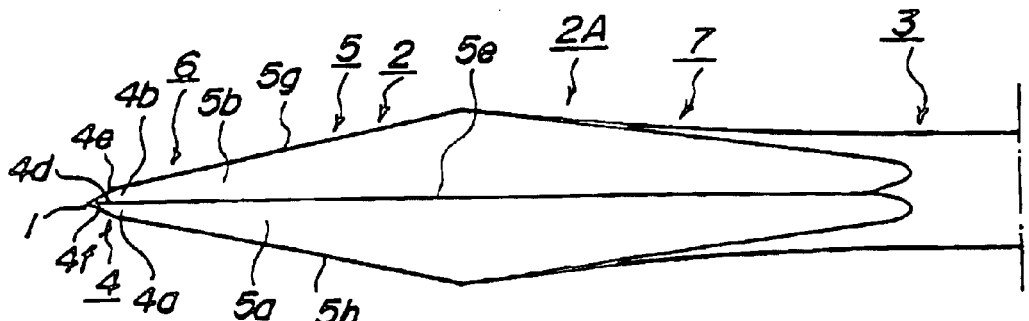
Figure 3:
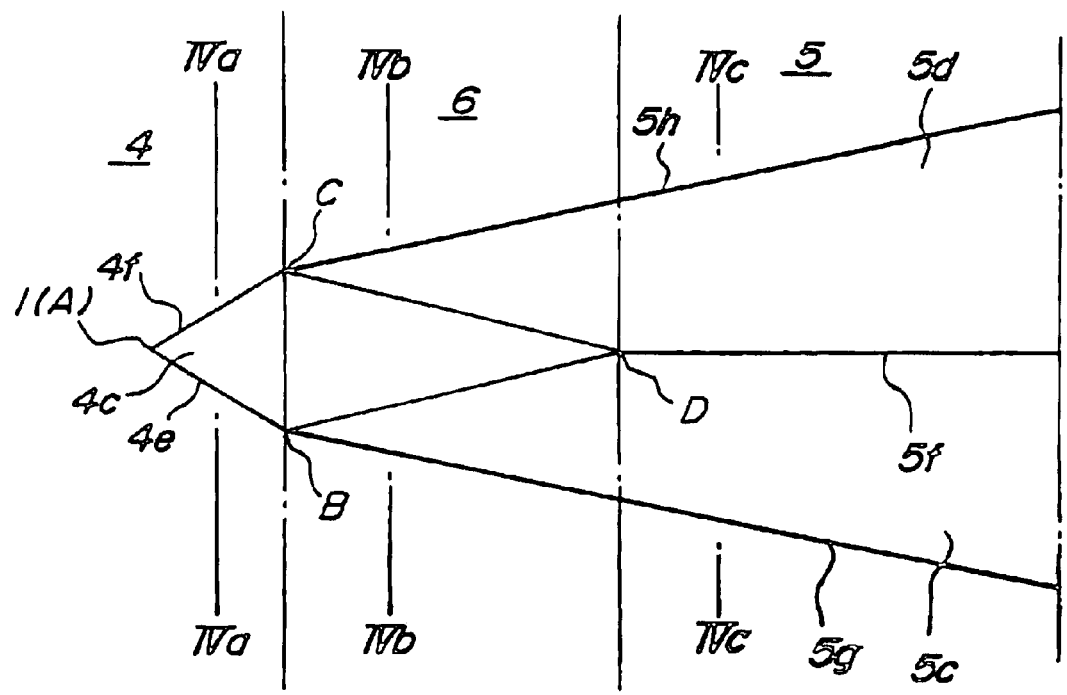
FIG. 3 is an enlarged view of a cutting blade portion.
Figure 4A:
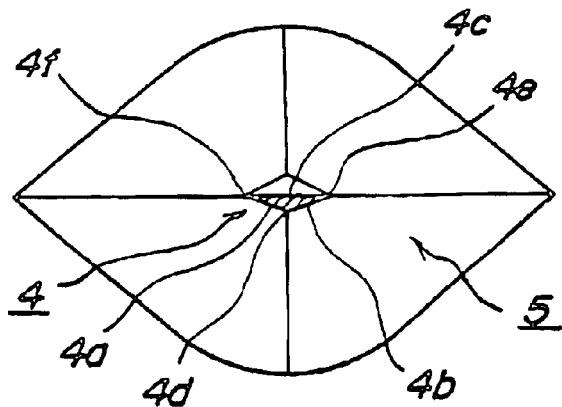
FIG. 4 is a view for explaining a cross-sectional shape of a cutting blade portion corresponding to the cross-sections for IVa, IVb, and IVc shown in FIG. 3.

A first preferable embodiment of a medical knife (bladed device), which is employed as the aforementioned bladed device, used in ophthalmologic surgery will hereinafter be described with reference to the drawings. FIG. 1 is a front view for explaining the structure of a bladed device. FIG. 2 is a four-face view for explaining the shape of an essential portion of a bladed device. FIG. 3 is an enlarged view of a cutting blade portion. FIG. 4 is a view for explaining a cross-sectional shape of a cutting blade portion corresponding to the cross-sections for IVa, IVb, and IVc shown in FIG. 3. FIG. 5 is a view for explaining a tip angle and a blade angle of a cutting blade portion.

The present invention related to a medical bladed knife has the functions of piercing a targeted affected area such as an eyeball, forming a primary incision, incising an affected area along a living body tissue starting from the primary incision, and widening the affected area, in which the medical bladed device can be favorably employed to a medical knife used in ophthalmologic surgery for incising the cornea or a space between the cornea and the sclera, or employed to an ophthalmologic suture needle for suturing an incised cornea. Nevertheless, the present invention is not be restricted to the foregoing usages, and can be favorably employed to a medical knife for piercing, incising, cutting-off or a suture needle for suturing an unstable affected area requiring delicate manipulation.

In the drawings, a bladed device A has a sharp tip 1, a cutting blade portion 2 formed from a point starting from the tip 1, and a shank portion 3 serving as a handle formed continuously from the cutting blade portion 2. The cutting blade portion 2 is divided into a tip-side cutting blade portion 4 formed from a point starting from the tip 1 and a shank-side cutting blade portion 5 formed proximal to the shank 3, in which an intermediary cutting blade portion 6 is formed between the cutting blade portions 4 and 5. A connection portion 7 having no function of cutting-open is formed between the cutting blade portion 2 and the shank portion 3.

The shank portion 3 is a portion where a physician grips during an operation, and is formed into an optimum shape and structure according to the function of the object medical bladed device. That is, the shank portion 3 is a portion inserted through and fixed to a handle (not shown) aimed to be gripped and manipulated by a physician when the bladed device A of this embodiment is employed as the object medical bladed device. In such case, the shank 3 is shaped as a round rod or a rectangular rod and, for example, is inserted through and fixed to a synthetic resin handle, or formed into a united body with the handle by insertion molding. When the object medical bladed device is a suture needle, the shank portion 3 has a means for attaching a suture thread to an end portion thereof and is formed into a round rod-like shape being curved in a prescribed curvature.

The connection portion 7 functions to connect the cutting blade portion 2 having a quadrangular shaped (including a rhombus shape) cross section and the shank portion 3 having a round or rectangular shaped cross section, in which the cross sectional shape of the cutting blade portion 2 formed into an optimum shape in accordance with the affected area targeted for incision and the cross sectional shape of the shank portion 3 are connected in a smooth, continuous manner, thereby force applied from a physician or counter-force arisen during incision can be transmitted without having stress from concentrating partially.

Accordingly, the cross sectional shape and measurement (e.g., length) of the connection portion 7 are determined in correspondence with the cross sectional shape of the cutting blade portion 2 and the cross sectional shape of the shank portion 3, and cannot be predetermined to a unique cross sectional shape nor measurement.

The ridgelines of the three faces 4a to 4c of the tip-side cutting blade portion 4, that is, a back 4d and a pair of secondary cutting blades 4e. 4f are intersected to form the tip 1. Forming the tip 1 with the back 4d and the cutting blades 4e, 4f in an intersected manner enables the tip 1 to be molded into a sharp pointed end having 3 ridgelines precisely matched with each other, and also serves to reduce pierce counterforce arisen during piercing of a living body tissue. It is now to be noted that the face 4c serves as a fifth face continuing to a first face 5a through a fourth face 5d (described afterwards).

The tip-side cutting blade portion 4a is formed with a prescribed length starting from the tip 1 and has a triangular cross section. The triangular cross section is comprised of two adjacent faces 4a, 4b with the back 4d arranged therebetween and the face 4c, in which the face form the long side of a triangle and, together with the faces 4a, 4b form the two cutting blades 4e, 4f.

The back 4d formed by the faces 4b and 4c has no function of incising a targeted living body tissue, but functions to widen the living body tissue incised by the cutting blades 4e and 4f. Therefore the back 4d does not require being shaped as a sharp edge.

The cutting blade 4e formed by the faces 4b and 4c and the cutting blade 4f formed by the faces 4c and 4a have a function of cutting open the targeted living body tissue and forming an incision, and are therefore formed with an optimum angle for cutting open the living body tissue, respectively. However, the angle for each of the cutting blades 4e, 4f is not to be restricted in particular, and is set with an optimum angle according to the living body tissue targeted for incision. For example, the optimum angle for each of the cutting blades 4e, 4f (secondary cutting blade angle) is approximately 50 degrees to 65 degrees when the incision target is an eyeball, e.g., cornea (knife for corneal incision).

The two cutting blade 4e, 4f of the tip-side cutting blade portion 4 have the tip 1 serving as a peak thereof and are intersected to form an angle β, in which the intersecting angle β serves as the tip angle. The angle β is a projection angle with respect to a plane passing through a center axis of the bladed device A. More particularly, since the face 4c of the tip-side cutting blade portion 4 is slightly inclined with respect to the center axis, the precise angle of the cutting blades 4e, 4f slightly changes in correspondence to the inclined angle. Nevertheless, such change is slight, and the angle for the two cutting blades 4e, 4f of the tip-side cutting blade portion 4, that is, the tip angle may be defined as angle β.

In forming the tip-side cutting blade portion 4 of this embodiment, a preformed shank-side cutting blade portion 5 is grinded with respect to the face 4c. Accordingly, the tip angle β can be set by altering the inclined angle of the face 4c with respect to the center axis of the bladed device A. That is, the tip angle β is set by defining a blade angle α formed by a pair of primary cutting blades 5g, 5h of the shank-side cutting blade portion 5 and also defining the inclined angle of the face 4c with respect to a plane which passes through the center axis of the bladed device A and includes the primary cutting blades 5g, 5h.

The tip angle β formed by the two cutting blades 4e and 4f of the tip-side cutting blade portion 4 is a factor having a large influence on pierce counterforce arisen during forming of a primary incision to a targeted affected area of a living body tissue. As shown in the data of the foregoing experiment the tip angle β is preferable to be small when piercing performance is only considered. However, the tip angle β is to be considered in combination with the blade angle α (described afterwards) since incision counterforce arisen in an incising procedure subsequent to the forming of the primary incision and inflexibility during the incising procedure are also included in judging the cutting performance of bladed device A.

The shank-side cutting blade portion 5 is formed more proximal toward the shank portion 3 compared to the tip-side cutting blade portion 4, in which a cross-sectional shape thereof is formed into a quadrangular shape having four faces 5a to 5d, and four ridgelines comprised of a back 5e formed between the adjacent faces 5a (first face 5a), 5b (second face 5b) on a back face 5B of the cutting blade portion 5, a back 5f formed between the adjacent faces 5c (third face 5c) and 5d (fourth face 5d) on a front face 5A, and the pair of primary cutting blades 5g, 5h formed between the adjacent faces 5b, 5c and 5d, 5a, respectively.

The faces 5a and 5b of the shank-side cutting blade portion 5 are formed continuously to the faces 4a and 4b of the tip-side cutting blade portion 4, and the back 5e formed between the faces 5a and 5b is also formed as a ridgeline continuing to the back 4d. That is, the face 5a and the face 4a, the face 5b and the face 4b, and the back 5e and the back 4e of the shank-side cutting blade portion 5 and the tip-side cutting. blade portion 4 are formed as continuous faces and backs, respectively, and are not to be separate.

Each of the ridgelines 5e to 5h of the shank-side cutting blade portion 5 are formed on the two perpendicularly intersecting planes passing through the center axis of the bladed device A. The backs 5e and 5f forming the ridgelines have no function of cutting open a targeted living body tissue, but function to widen the living body tissue incised by the cutting blades 5g and 5h. Therefore, the backs 5e and 5f do not require being shaped as sharp edges.

The cutting blade 5g formed by the faces 5b and 5c and the cutting blade 5h formed by the faces 5d and 5a function to cutting open the targeted living body tissue and form an incision, and are therefore formed with an optimum angle for cutting open the living body tissue, respectively. The angle for each of the cutting blades 5g, 5h is not to be restricted in particular, and is set with an optimum angle according to the: living body tissue targeted for incising. However, the angle for each of the cutting blades 5g, 5h, obviously, is not the same as that for the cutting blades 4e, 4f of the tip-side cutting blade portion 4.

Each of the cutting blades 5g and 5h of the shank-side cutting blade portion 5 are formed continuously to each of the cutting blades 4e and 4f of the tip-side cutting blade portion 4, thereby, the cutting blades 5g, 4e, 5h, 4f of the cutting blade portions 4 and 5 are formed starting from the tip 1 and continuing across the entire length of the cutting blade portion 2 to enable satisfactory cutting performance.

The two cutting blades 5g and 5h of the shank-side cutting blade portion 5 form an angle, in which the two cutting blades 5g and 5h are arranged approaching toward each other into the direction of the tip-side. That is, the two cutting blades 5g and 5h are arranged to intersect in an angle a (blade angle) at an imaginary intersecting point X extending further than the tip 1 of the bladed device A as shown in FIG. 5.

That is, the fifth face 4c, which is formed to allow the cutting blade portion 3 to diagonally incise from a front face 2B to a back face 2A, is formed into a quadrangular shaped face by connecting intersecting points A, B, C and D, in which the tip 1 (A) is the intersecting point with respect to the ridgeline 5e of the back face 2A, numeral B and numeral C are the intersecting points with respect to the pair of primary cutting blades 5g, 5h, and numeral D is the intersecting point with respect to the ridgeline 5f of the front face 2B. The angle formed by the secondary cutting blades 4e, 4f (secondary cutting blade angle BAC: α) is set with an angle larger than that of the angle formed by the primary cutting blades 5h, 5g (primary cutting blade angle BXC: β).

As shown in the data of the foregoing experiment, the blade angle α of the two cutting blades 5g and 5h of the shank-side cutting blade portion 5 has a large influence on incision counterforce arisen during an incision procedure subsequent to the forming of a primary incision with the tip-side cutting blade portion 4. That is, the incision counterforce becomes smaller as the blade angle α becomes smaller, and becomes larger as the blade angle α becomes larger. However, there is a large possibility that inflexibility would decrease when the blade angle α becomes smaller.

Considering such possibility, the tip angle β of the bladed device A is set to have a difference ranging from 20 degrees to 70 degrees in relation to the blade angle α. However, the value of the blade angle α is not to be restricted from 20 degrees to 30 degrees as in the data of the foregoing experiment, and can also be set to a degree where the two blade cutting blades 5g and 5h are almost parallel. Even when the blade angle α formed by the two blade cutting blades 5g and 5h of the shank cutting blade portion 5 is set to a degree where the two blade cutting blades 5g and 5h are almost parallel, the tip 1, which has three ridgelines comprised of two cutting blades 4e and 4f and the back 4d, can be formed by forming the fifth face 4c on the tip-side cutting blade portion under the condition that the cross section of the shank cutting blade portion 5 has a quadrangular shape.

However, when the blade angle α is smaller than 15 degrees, low inflexibility may adversely affect manipulability during piercing and incising of the living body tissue with the blade device A.

Figure 4B:
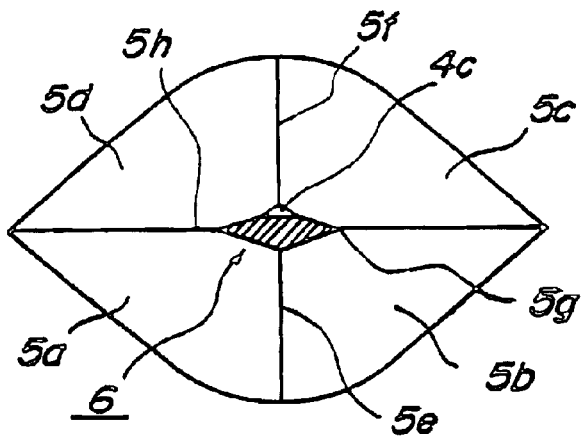
Figure 4C:
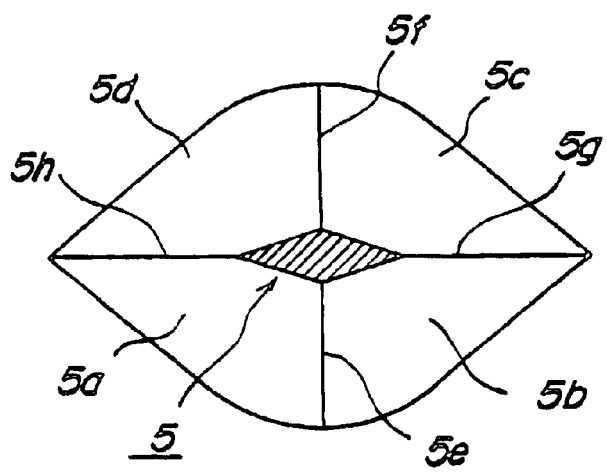
Figure 5:
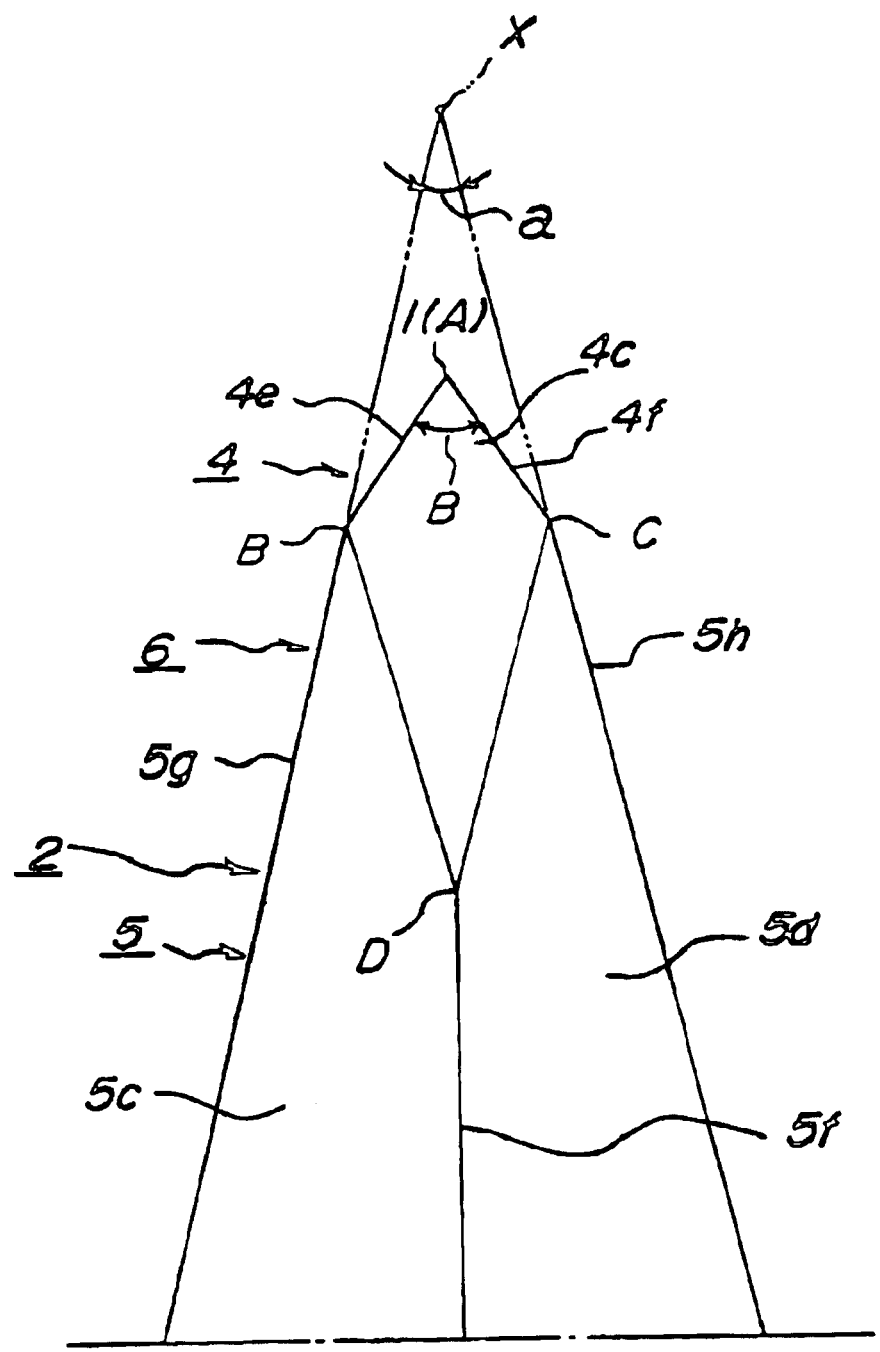
FIG. 5 is a view for explaining a tip angle and a blade angle of a cutting blade portion.

The intermediary cutting blade portion 6 is a portion where the face 4c of the tip-side cutting blade portion 4 intersects with the two cutting blades 5g, 5h and the back 5f of the shank-side cutting blade portion 5, in which the intermediary cutting blade portion 6 has a pentangular cross section comprised of the faces 5a to 5d of the shank-side cutting blade portion 5 and the face 4c of the tip-side cutting blade portion 4 as shown in FIG. 4(b). The cutting blades 5g and 5h, while continuing to function as cutting blades, are connected to the cutting blades 4e and 4f of the tip-side cutting blade portion 4.

In forming the foregoing bladed device A, a round rod is pressed and a rough shape of the shank portion 3, the shank-side cutting blade portion 5, and the connection portion 7 is molded. The rough shape of the shank-side cutting blade portion is molded in a manner where a portion corresponding to the two cutting blades 5g, 5h is formed with a predetermined blade angle α. Therefore, a blank of the bladed device A is formed with a sharp tip portion reaching the imaginary intersection point X. Each of the faces 5a to 5d of the shank cutting blade portion 5 are formed by grinding or polishing the blank, and the two backs 6e, 5f and the two cutting blades 5g, 5h are also formed in association with such forming of the faces 5a to 5d. The blank can be polished or grinded in a direction intersecting to the cutting blades 5g, 5h, in particular, can be perpendicularly intersecting to the cutting blades 5g, 5h, or in a axial direction of the bladed device A.

Subsequent to forming the portion corresponding to the shank-side cutting blade portion 5, the faces 5c and 5d of the shank-side cutting blade portion 5 including the back 5f are grinded, the face 4c of the tip-side cutting blade portion 4 is formed from such grinded face, and further in association with the grinding of the face 4c, the cutting blade 4e is formed between the face 4c and the face 4b, and the cutting blade 4f is formed between the face 4c and the face 4a; thereby, the three ridgelines consisted of the two cutting blades 4e, 4f, and the back 4d are matched to form the tip 1.

Defining the inclined angle of the face 4c with respect to the center axis of the bladed device A during the forming of the face 4c and the tip-side cutting blade 4 allows the tip angle β formed by the two cutting blades 4e and 4f to be set selectively.

A round rod is not necessarily required to be press molded in forming the bladed device A, but also a board member can be cut or stamped out by pressing in producing a material targeted for grinding. In such case, the strength of the material should preferably increased by heat processing before the cutting blade(s) are formed by grinding or polishing.

More particularly, an austenitic stainless steel is a preferable material in forming the bladed device by press processing a round rod. With such material, work hardening can be expected in association with the press process and strength can be increased uniformly without requiring heat processing. A martensitic stainless steel is a preferable material in processing a board material for forming the bladed device A and in increasing the strength by heat processing.

Nevertheless, the material of the present invention is not to be restricted, and each kind of the aforementioned stainless steel or titanium having excellent compatibility to a living body can also be used.

When the range in the difference between the tip angle β and the blade angle α is in the range of 20 degrees to 70 degrees as in the present invention, both cutting performance and endurance are satisfactory, and the bladed knife A can be formed having an angle combination of any kind within such range. The difference between the tip angle β and the blade angle α should preferably be set within the foregoing range according to circumstance, that is depending on, for example, the material of the bladed device A or the use of the medical bladed device (a knife or a suture needle).

According to the finding(s) of the present inventor(s), both cutting performance and endurance can be maintained at a high level to allow satisfactory results whether the medical bladed device is a knife or a suture needle under the condition that the difference between the tip angle β and the blade angle α is within the range of 30 degrees to 60 degrees.

Figure 6:
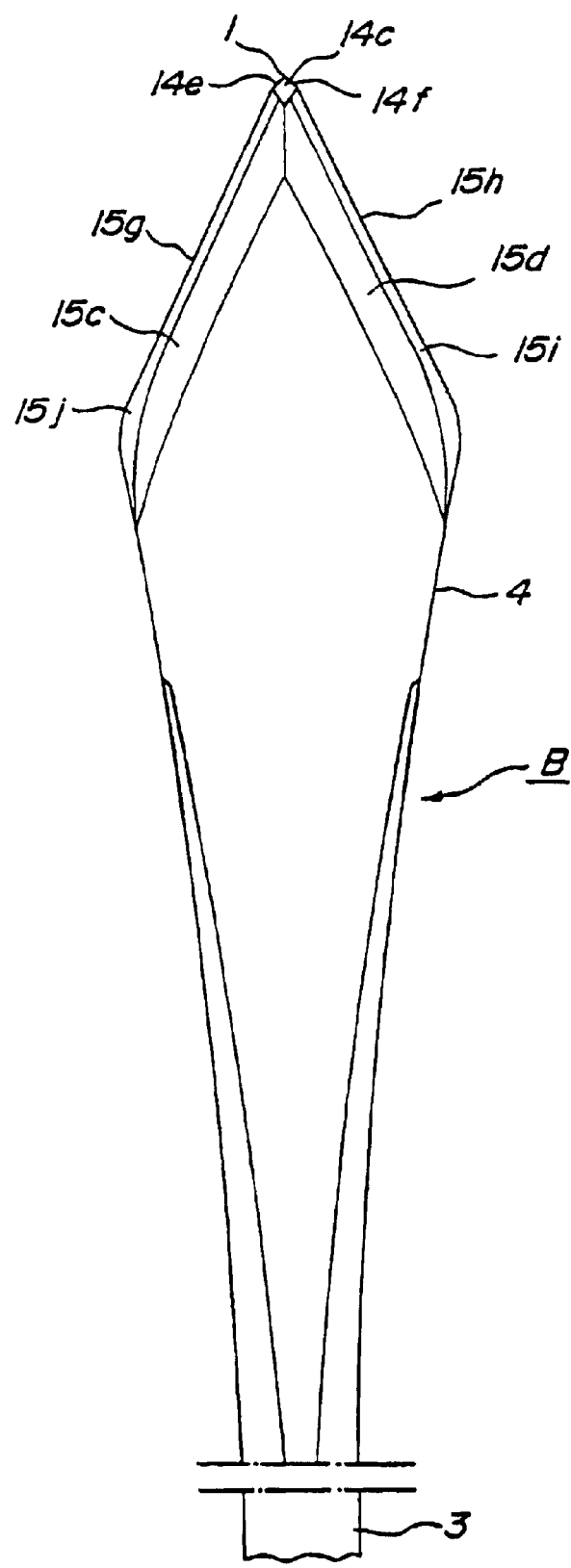
FIG. 6 is a plan view of a back face side of a medical bladed device.

A second embodiment of this invention will be described with reference to FIG. 6. FIG. 6 is a plan view of a back face side of a medical bladed device for the second embodiment of this invention.

As shown in the FIG. 6, a bladed device B, subsequent to incising the surface of an eyeball, serves to widen the incised portion to a width of an intraocular lens folded for insertion into the eye, and has a cutting blade portion 4 formed in a manner similar to the bladed device A of the first embodiment, in which the cutting blade portion 4 is arranged on one end of a shank portion 3 serving as a handle.

The cutting blade portion 4 has a sharp tip formed into a rhombus shape, in which the tip has a pair of primary cutting blades 15g, 15h formed on two sides thereof being shaped by grinding the front face and the back face, and by grinding a first face (not shown), a second face (not shown) and also a third face 15c, a fourth face 15d along the two sides, respectively. The first face to the fourth face are ground in two levels to form different angle, so that the bent portions 15i, 15j are formed in a manner adjacent to the primary cutting blade portions 15g, 15h.

Although having a smaller area compared to that of the bladed device A of the first embodiment, a fifth face 14c having a taper tip 1 is ground and formed at a tip portion. In processing the fifth face 14c, two sides arranged proximal to the tip portion of the rhombus shaped fifth face 4c have a pair of secondary cutting blades 14e, 14f formed thereto. Considering the relation with cutting performance and inflexibility, the primary cutting blade angle formed by the pair of primary cutting blades 15g, 15h and an imaginary intersecting point (not shown) is set from 40 degrees to 55 degrees, and the secondary cutting blade angle formed by the pair of secondary cutting blades 14e, 14f and the tip 1 is set from 90 degrees to 100 degrees.

In a similar manner as the first embodiment, a desirable bladed device with respect to cutting performance and inflexibility can be provided by setting the relation between the primary cutting blade angle and the secondary cutting blade angle for the cutting blade B in accordance with the foregoing range.

Factor(s) such as the angle for contacting a grindstone upon a targeted grinding face, the pressing force against the grindstone, or time, should preferably be controlled appropriately when grinding each of the faces during the forming of the tip-side cutting blade 4 and the shank-side cutting blade 5. More particularly, the granularity of the grindstone should preferably be selected in accordance to material.

The bladed device A should preferably be clean and smooth for enhancing cutting performance. The bladed device A may preferably be applied with electrolytic polishing or chemical polishing, or applied with a silicone coating on a surface thereof. When the bladed device A is employed for an operation by observing an affected area with a microscope, the bladed device A may preferably be applied with a non-glare finish. More particularly, a non-glare finish should preferably be applied at least to the fifth face 4c, 14c since the fifth face 4c, 14c is formed with an angle different from the faces. To be more specific, the non-glare finish is performed such as by sandblasting, so that the surface is roughened to provide a lacquered-like finish.

Such treatment applied for the surface of the bladed device of the present invention is not to be restricted in particular, and can be applied according to necessity.

With the present invention related to a medical bladed device, a cutting blade portion has a tip-side thereof formed with a triangular shaped cross section and a shank-side thereof formed with a quadrangular shaped cross section, and the difference between a tip angle formed by two cutting blades on the tip-side and a blade angle formed by two cutting blades on the shank-side is set to range from 20 degrees to 70 degrees to allow a tip to be matched precisely at a single peak, thereby, piercing performance can be enhanced and cutting performance including piercing performance and incising performance can also be enhanced. Further, inflexibility during in an incising procedure can be increased and results to enhancement in the strength of the cutting blade portion, manipulability, and endurance.

Manufacture cost can be prevented and a firm bladed device can be manufactured since the cutting blade portion of the tip-side can be formed by grinding or polishing a single face of the cutting blade portion of the shank-side.

The foregoing description of a preferred embodiment of the invention has been presented for purposes of illustration and description, and is not intended to be exhaustive or to limit the invention to the precise form disclosed. The description was selected to best explain the principles of the invention and their practical application to enable others skilled in the art to best utilize the invention in various embodiments and various modifications as are suited to the particular use contemplated. It is intended that the scope of the invention not be limited by the specification, but be defined by the claims set forth below.

What is claimed is:

1. A medical bladed device comprising:
   a handle; and
   a cutting blade portion being tapered and formed in continuation from the handle, wherein the cutting blade portion comprises:
   a front face comprised of a first face and a second face, said first face having a first side, a back end and a front end, said second face having a first side, a back end and a front end, said first face and said second face being formed on two perpendicularly intersecting planes passing through a center axis of the bladed device, the front end of said first face and said front end of said second face intersecting to form a front face intersection
   a back face comprised of a third face and a fourth face, said third face having a first side, a back end and a front end, said fourth face having a first side, a back end and a front end, said first face and said second face being formed on two perpendicularly intersecting planes passing through a center axis of the bladed device, said front end of said third face and said front end of said fourth face intersecting to form a back face intersection;
   a pair of primary cutting blades, each of said primary cutting blades having a primary cutting blade front end and a primary cutting blade back end, each of said primary cutting blades being formed on the first sides of said front face and back face,
   a pair of secondary cutting blades, each of said secondary cutting blades having a secondary cutting blade front end and a secondary blade back end, the secondary cutting blade back ends intersecting with the primary blade front ends of the primary cutting blades, the secondary cutting blade front ends intersecting with each other, each of said secondary cutting blades being formed on both sides of said front face and back face;
   a sharp tip formed at the intersection of said secondary cutting blade front ends adjacent the front face; and
   a square-shaped fifth face having a triangular cross section defined by the front face intersection, the pair of secondary cutting blades and the sharp tip,
   wherein a secondary cutting blade angle formed by the pair of secondary cutting blades ranges from 35 degrees to 105 degrees, and a primary cutting blade angle formed by an imaginary intersecting point between the pair of primary cutting blades ranges from 15 degrees to 35 degrees.

2. The medical bladed device according to claim 1, wherein the difference between the secondary cutting blade angle and the primary cutting blade angle ranges from 30 degrees to 60 degrees.

3. The medical bladed device according to claim 1, wherein the secondary cutting blade angle ranges from 50 degrees to 60 degrees and the primary cutting blade angle ranges from 20 degrees and 30 degrees.

4. The medical bladed device according to claim 1, wherein the secondary cutting blade angle ranges from 90 degrees to 110 degrees and the primary cutting blade angle ranges from 40 degrees and 55 degrees.

5. The medical bladed device according to claim 1, wherein an anti-glare finish is applied at least to the fifth face.

6. The medical bladed device according to claim 1, wherein the primary cutting blade is ground in a direction intersecting with the primary cutting blade.

7. The medical bladed device according to claim 1, wherein the cutting blade portion has a bordering portion between the first face and the second face formed without an edge, and a bordering portion between the third face and the fourth face formed without an edge.

8. A medical bladed device comprising:
   a handle; and
   a cutting blade portion being tapered and continuing from the handle, wherein the cutting blade portion is comprised of:
   a front face comprised of a first face and a second face, said first face having a first side, a back end and a front end, said second face having a first side, a back end and a front end, said first face and said second face being formed on two perpendicularly intersecting planes passing through a center axis of the bladed device, the front end of said first face and said front end of said second face intersecting to form a front face intersection;
   a back face comprised of a third face and a fourth face, said third face having a first side, a back end and a front end, said fourth face having a first side, a back end and a front end, said first face and said second face being formed on two perpendicularly intersecting planes passing through a center axis of the bladed device, said front end of said third face and said front end of said fourth face intersecting to form a back face intersection;
   a pair of primary cutting blades, each of said primary cutting blades having a primary cutting blade front end and a primary cutting blade back end, each of said primary cutting blades being formed on the first sides of said front face and back face;
   a pair of secondary cutting blades, each of said secondary cutting blades having a secondary cutting blade front end and a secondary blade back end, the secondary cutting blade back ends intersecting with the primary blade front ends of the primary cutting blades, the secondary cutting blade front ends intersecting with each other, each of said secondary cutting blades being formed on both sides thereof of said front face and back face;

a sharp tip formed at the intersection of said secondary cutting blade front ends adjacent the front face; and a square-shaped fifth face having a triangular cross section defined by the front face intersection, the pair of secondary cutting blades and the sharp tip, wherein an angle formed by the secondary cutting blade and the tip is larger than an angle formed by the primary cutting blade and an imaginary intersecting point, and the difference between both angles ranges from 20 degrees to 70 degrees.

* * * * *